United States Patent
Buehler et al.

(10) Patent No.: US 7,527,652 B2
(45) Date of Patent: May 5, 2009

(54) DITHIOL COMPOSITIONS AND METHODS OF TREATING ANIMAL HIDES USING THE SAME

(75) Inventors: Holger Buehler, Altrip (DE); Joaquim Henrique Teles, Otterstadt (DE); Gunther Pabst, Neumarkt i. d. OPf. (DE); Tilman Luedecke Taeger, Seeheim-Jugenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 161 days.

(21) Appl. No.: 10/571,772

(22) PCT Filed: Sep. 10, 2004

(86) PCT No.: PCT/EP2004/010123

§ 371 (c)(1), (2), (4) Date: Mar. 15, 2006

(87) PCT Pub. No.: WO2005/033070

PCT Pub. Date: Apr. 14, 2005

(65) Prior Publication Data

US 2006/0277687 A1    Dec. 14, 2006

(30) Foreign Application Priority Data

Sep. 17, 2003    (DE) ................. 103 43 252

(51) Int. Cl.
*C14C 1/00*    (2006.01)
*C07D 301/12*    (2006.01)
*C07C 323/02*    (2006.01)
*C07F 11/00*    (2006.01)

(52) U.S. Cl. .................. 8/94.15; 568/62; 540/465; 549/531

(58) Field of Classification Search ........... 8/94.15; 568/62
See application file for complete search history.

(56) References Cited

U.S. PATENT DOCUMENTS 5,329,024 A    7/1994    Jureller et al.
6,706,077 B2 *    3/2004    Bhagyalakshmi et al. ...... 8/405

FOREIGN PATENT DOCUMENTS

DE    21 31 630    1/1972
DE    2 209 458    9/1972
DE    2 337 101    1/1974

OTHER PUBLICATIONS

De Vos, Dirk E. et al., "Epoxidation of Terminal or Electron-deficient Olefins with H2o2, catalysed by Mn-trimethyltriazacyclonane, Complexes in the Presence of an Oxalate Buffer", Tetrahedron Letters, vol. 39, No. 20, pp. 3221-3224, 1998.
Cleland W.W., Dithiothreitol, a New Protective Reagent for SH Groups, Biochemistry, vol. 3 No. 4, pp. 480-482, 1964.

* cited by examiner

*Primary Examiner*—Rei-Tsang Shiao
*Assistant Examiner*—Yong Chu
(74) *Attorney, Agent, or Firm*—Oblon, Spivak, McClelland, Maier & Neustadt, P.C.

(57) ABSTRACT

Mixtures of (A) from 55 to 65 mol % of erythro-dithiol of formula erythro-IV:

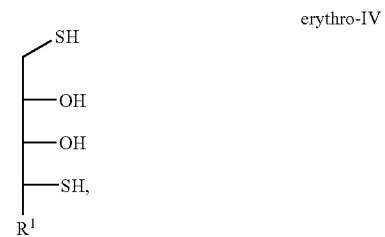

and
(B) from 35 to 45 mol % of threo-dithiol of formula threo-IV or threo-IV':

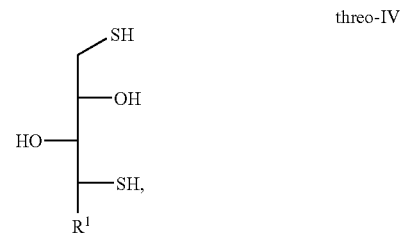

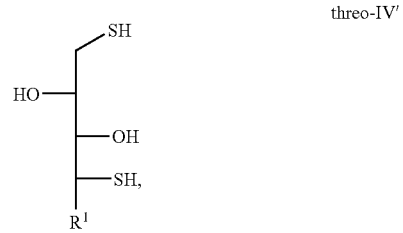

and their corresponding alkali metal salts and ammonium salts, are useful for treating animal hides.

14 Claims, No Drawings

DITHIOL COMPOSITIONS AND METHODS OF TREATING ANIMAL HIDES USING THE SAME

CROSS REFERENCE TO RELATED APPLICATION

This application is a 371 of PCT/EPO4/10123, filed on Sep. 10, 2004, and claims priority of Germany Patent Application No. 103 43 252.3, filed on Sep. 17, 2003.

The present invention relates to a process for the preparation of bisepoxides, wherein a conjugated diene of the formula I

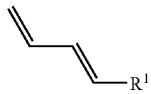

where
$R^1$ is selected from hydrogen and $C_1$-$C_{12}$-alkyl, unsubstituted or substituted by one or more S—H or O—H groups,
is reacted in the presence of a catalyst which is obtainable by bringing
at least one manganese compound selected from $A_2MnX_4$, $AMnX_3$, $MnY$, $MnX_2$ and $MnX_3$ into contact
with at least one ligand L of the formula II

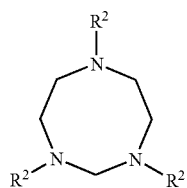

where
X are identical or different and are selected from monovalent anions,
Y is a divalent anion,
A is selected from alkali metal and ammonium, which may be alkylated, and
$R^2$ are different or preferably identical and are selected from $C_1$-$C_{20}$-alkyl and at least one coligand which is derived from monocarboxylic acids, dibasic or polybasic carboxylic acids or diamines,
with at least one peroxide, up to 4 equivalents of peroxide being used per equivalent of C—C double bond.

Dithiols are extremely versatile reagents. Thus, it is known that 1,4 dimercaptobutanediol can be used in the purification and stabilization of enzymes (protective reagents for —SH groups, W. W. Cleland, *Biochemistry*, 3 (1964), 480). Furthermore, DE 22 09 458 discloses that so-called 1,4-dithiol-2,3-butanediol and its metal salts can be used as hair waving compositions and unhairing compositions. DE 23 37 101 discloses that n-butane-2,3-diol-1,4-dithiol and its alkali metal salts can be used for producing permanent waves. DE 21 31 630 discloses that compositions comprising at least 0.25% by weight of dimercaptobutanediol and from about 0.01 to 40% by weight of a water-soluble guanidine compound and having a pH of less than 12 can be applied to guinea pigs in order to unhair them or to human horny skin in order to eliminate calluses without resulting in skin irritations in guinea pigs or even erythremia (malignant proliferations of the formation system of the red blood corpuscles). The epidermis remains intact in the treatment described in DE 21 31 630.

It is therefore desirable to find a synthesis route by means of which n-butane-2,3-diol-1,4-dithiol and derivatives can be obtained with good yield and in good purity.

DE 22 09 458 and DE 23 37 101 disclose that racemic dithiolbutanediol, contaminated with slight amounts of dithioerythrol, can be prepared by reacting butadienebisepoxide with hydrogen sulfide in the presence of an alkaline catalyst in the range from 15 to 40° C. in a composition which dissolves hydrogen sulfide and whose volume is in the ratio of at least 5:1 to the volume of butadienebisepoxide, and isolating the dithiolbutanediol thus obtainable.

U.S. Pat. No. 5,329,024 discloses that olefins can be reacted in the presence of manganese complexes with the aid of large molar excesses of $H_2O_2$, for example olefin: $H_2O_2$=1:100) to give epoxides.

D. de Vos et al., *Tetrahedron Lett.* 39 (1998), 3221 disclose that bisepoxides of isoprene and of 4-vinylcyclohexene can be prepared by reacting the relevant dienes with a large excess (molar ratio about 12:1) of $H_2O_2$ in the presence of a manganese complex. In spite of the large excesses of $H_2O_2$, however, considerable amounts of monoepoxides are obtained. Furthermore, the yield of desired bisepoxide is still capable of improvement.

It is an object of the present invention to provide a process for the preparation of bisepoxides and dithiols in good yield and sufficient purity. It is a further object of the present invention to provide novel mixtures of dithiols and uses for mixtures of dithiols.

We have found that these objects are achieved by the process defined at the outset.

According to the invention, a conjugated diene of the formula I

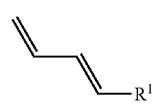

where
$R^1$ is selected from
$C_1$-$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl or n-decyl, particularly preferably $C_1$-$C_4$-alkyl, such as methyl, ethyl, n-propyl, isopropyl, n-butyl, isobutyl, sec-butyl and tert-butyl;
$C_1$-$C_{12}$-alkyl, substituted by one or more hydroxyl or thiol groups, such as hydroxymethyl, 2-hydroxyethyl, 1,2-dihydroxyethyl, 3-hydroxy-n-propyl, 2-hydroxyisopropyl, ω-hydroxy-n-butyl, ω-hydroxy-n-decyl, HS—$CH_2$—; HS—$(CH_2)_2$— or HS—$(CH_2)_3$—,
and very particularly preferably hydrogen, is reacted.

Of course, mixtures of olefins or dienes which comprise conjugated diene of the formula I can also be reacted.

According to the invention, the reaction is effected in the presence of a catalyst which is obtainable by bringing at least one manganese compound, selected from $A_2MnX_4$, $AMnX_3$, MnY, $MnX_2$ and $MnX_3$, into contact with at least one ligand L of the formula II

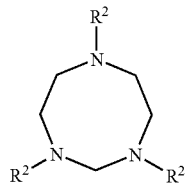

II and at least one coligand, which is derived from monocarboxylic acids, dibasic or polybasic carboxylic acids or diamines, where X are different or identical and are selected from monovalent anions, $R^3O^-$, $F^-$, $Cl^-$, $Br^-$, $I^-$, $NCS^-$, $N_3^-$, $I_3^-$, $R^3COO^-$, $R^3SO_3^-$, $R^3SO_4^-$, $OH^-$, $CN^-$, $OCN^-$, $NO_3^-$, $ClO_4^-$, $PF_6^-$, $BPh_4^-$, where Ph is phenyl and $F_3CSO_3^-$. $Cl^-$ and acetate are particularly preferred.

Y is a divalent anion, particularly preferably $SO_4^{2-}$ and $HPO_4^{2-}$.

A are different or preferably identical and are selected from alkali metal cations, for example $Li^+$, $Na^+$, $K^+$, $Rb^+$ and $Cs^+$, in particular $Na^+$ and $K^+$ and ammonium $NH_4^+$, which may be alkylated, for example $N(R^4)(R^5)(R^6)(R^7)^+$, where $R^4$ to $R^7$ are in each case identical or different and are selected from hydrogen, benzyl, $C_1$-$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl or n-decyl, particularly preferably $C_1$-$C_4$-alkyl, such as methyl, ethyl, n-propyl, isopropyl, n-butyl, isobutyl, sec-butyl and tert-butyl, phenyl or $CH_2$—$CH_2$—OH. Examples are tetramethylammonium, tetraethylammonium, methyldiethanolammonium and n-butyldiethanolammonium.

$R^2$ are different or preferably identical and are selected from branched or preferably straight-chain $C_1$-$C_{20}$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-octyl, n-decyl, n-dodecyl, n-tetradecyl, n-hexadecyl, n-octadecyl and n-eicosyl, preferably straight-chain $C_1$-$C_{12}$-alkyl, such as methyl, ethyl, n-propyl, n-butyl, n-pentyl, n-hexyl, n-heptyl, n-octyl, n-decyl or n-dodecyl, particularly preferably $C_1$-$C_4$-alkyl, such as methyl, ethyl, n-propyl, n-butyl, and very particularly preferably methyl.

$R^3$ is preferably $C_1$-$C_{20}$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-octyl, n-decyl, n-dodecyl, n-tetradecyl, n-hexadecyl, n-octadecyl and n-eicosyl, preferably straight-chain $C_1$-$C_{12}$-alkyl, such as methyl, ethyl, n-propyl, n-butyl, n-pentyl, n-hexyl, n-heptyl, n-octyl, n-decyl or n-dodecyl, particularly preferably $C_1$-$C_4$-alkyl, such as methyl, ethyl, n-propyl, n-butyl and very particularly preferably methyl, substituted $C_1$-$C_{20}$-alkyl, for example ω-cyclohexylpropyl, 2-cyclohexylethyl;

$C_3$-$C_{12}$-cycloalkyl, for example cyclopropyl, cyclobutyl, cyclopentyl, cyclohexyl, cycloheptyl, cyclooctyl, cyclononyl, cyclodecyl, cycloundecyl and cyclododecyl, preferably cyclopentyl, cyclohexyl and cycloheptyl;

$C_6$-$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl or benzyl.

Particularly preferred examples of manganese compounds used according to the invention are manganese(II) sulfate, manganese(II) acetate, manganese(II) chloride, manganese (I) perchlorate or potassium hexachloromanganate(IV) $K_2MnCl_6$.

It is possible for manganese compounds used according to the invention to have water of crystallization and/or water of hydration, for example $Mn(OAc)_2 \cdot 4H_2O$, $MnSO_4 \cdot H_2O$, $Mn(ClO_4)_2 \cdot 6H_2O$, $MnCl_2 \cdot 4H_2O$.

In an embodiment of the present invention, from 0.001 to 0.1, particularly preferably from 0.005 to 0.01, equivalent, based on diene of the formula I, of manganese compound is used.

In another embodiment of the present invention, form 0.00001 to 0.001, particularly preferably from 0.0001 to 0.0005, equivalent, based on dienne of the formula I, of manganese compound is used.

In an embodiment of the present invention, from 1 to 5, preferably from 1.1 to 2, equivalents, based on manganese, of ligand L of the formula II are used.

Suitable coligands are those compounds which are derived from monocarboxylic acids, dibasic or polybasic carboxylic acids or diamines, i.e. monocarboxylic acids, dibasic or polybasic carboxylic acids and diamines themselves and, in the case of monocarboxylic acids and dibasic or polybasic carboxylic acids, in particular their corresponding alkali metal salts.

In an embodiment of the present invention, coligands are derived from such monocarboxylic acids or dibasic or polybasic carboxylic acids whose $pK_a$ or $pK_a^1$ value in water at 25° C. is less than 7.

In an embodiment of the present invention, coligands are derived from oxalic acid (III.1) dihydroxyfumaric acid (III.2), tartaric acid (III.3), maleic acid (III.4), squaric acid (III.5), 2-sulfobenzoic acid (III.6) and N(p-toluenesulfonyl)glycine (III.7):

III.1

III.2

III.3

III.4

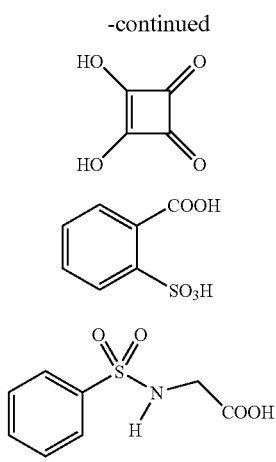

Ascorbic acid is furthermore suitable.

A further very particularly preferred coligand is 1,2-diaminocyclohexane, both the isomer mixture and the respective cis- and trans-isomers in enriched form being suitable.

In an embodiment of the present invention, coligands are used in the form of a mixture of monocarboxylic acids and alkali metal salt of the relevant monocarboxylic acid.

In an embodiment of the present invention, coligands are used in the form of a mixture of dibasic or polybasic carboxylic acid and alkali metal salt of the relevant dibasic or polybasic carboxylic acid.

In an embodiment of the present invention, from 0.1 to 5 equivalents, preferably from 0.5 to 1 equivalent, based on manganese, of coligand are used.

According to the invention, diene of the formula I is reacted with at least one peroxide, up to 4 equivalents of peroxide being used per equivalent of C—C double bond. Preferably, at least one equivalent of peroxide is used per equivalent of C—C double bond. Preferably organic peroxides, in particular tert-butyl hydroperoxide, cumyl hydroperoxide, 1,3-diisopropyl monohydroperoxide or 1-phenylethyl hydroperoxide, are used as the peroxide. Hydrogen peroxide ($H_2O_2$) is particularly preferred as the peroxide.

If it is desired to use hydrogen peroxide, it is employed as an aqueous solution, for example as a 30% by weight or 50% by weight solution whose content of reactive $H_2O_2$ can be determined by known methods, for example by titration.

In an embodiment of the present invention, up to 3, preferably up to 2.1, equivalents of peroxide are used per equivalent of C—C double bond.

Several procedures are possible for the order in which the reactants of the novel process are brought into contact.

In one embodiment of the present invention, ligand L of the formula II and coligand are first mixed with diene of the formula I and peroxide, and manganese compound is then added.

In another embodiment of the present invention, ligand L of the formula II is first mixed with coligand and diene of the formula I and manganese compound, and peroxide is then added.

In another embodiment of the present invention, a complex compound is first prepared by bringing manganese compound and ligand L and coligand of the formula II into contact and is then mixed with diene of the formula I and then with peroxide.

In another embodiment of the present invention, a complex compound is first prepared by bringing manganese compound and ligand L of the formula II into contact and is then mixed with diene of the formula I and coligand and then with peroxide.

In another embodiment of the present invention, a complex compound of the formula $[LMn(\mu\text{-}O)_3MnL]X$ is first prepared by bringing manganese compound and ligand L of the formula II into contact and is then mixed with diene of the formula I and coligand and then with peroxide.

In another embodiment of the present invention, a complex compound is first prepared by bringing manganese compound and ligand L and coligand of the formula II into contact and is then mixed with diene of the formula I and then with peroxide, peroxide being added in two portions at a time interval of at least 2 hours.

The form in which the catalytically active species is present is not known exactly. Without wishing to give preference to one theory, it appears conceivable that manganese is present at least from time to time in the oxidation state +IV during the catalytic reaction. Furthermore, it appears possible that singly or multiply μ-oxo-bridged species are present at least from time to time during the catalytic reaction.

In an embodiment of the present invention, the novel process is carried out in a solvent or a mixture of solvents. Solvents used may be organic or inorganic liquids which are liquid at room temperature and, under the conditions, react only in negligible proportions, if at all, with the reactants and product, i.e. for example bisepoxide.

For example, $C_1$-$C_4$-alkanols, such as methanol, ethanol, n-propanol or isopropanol, and furthermore ketones, for example acetone, methyl ethyl ketone and methyl isobutyl ketone (MIBK), acetonitrile, halogenated hydrocarbon, for example methylene chloride, chloroform or 1,1,2,2-tetrachloroethane, and water are suitable. Mixtures of water and acetonitrile, mixtures of water and methanol and mixtures of water and acetone are particularly suitable.

In an embodiment of the present invention, a solvent or mixture of solvents is used in an amount such that the concentration of bisepoxide does not exceed 50% by weight and is preferably from 5 to 15% by weight.

In an embodiment of the present invention, the novel process is carried out without having immobilized the catalyst beforehand on one or more solid support materials, for example silica gel or alumina.

In an embodiment of the present invention, the novel process is carried out at temperatures in the range from −50 to 100° C., preferably from −30 to 80° C., particularly preferably from −10 to 60° C. and very particularly preferably from 0 to 5° C.

In an embodiment of the present invention, the novel process is carried out under a pressure in the range from 1 to 200, preferably from 1 to 100, bar, particularly preferably at from atmospheric pressure to 10 bar.

In an embodiment of the present invention, the novel process is carried out at a pH of from 1 to 7, preferably from 3 to 5.

In an embodiment of the present invention, the duration of the reaction is from 1 minute to 24 hours, preferably from 30 minutes to 20 hours.

Suitable reaction vessels for carrying out the novel process are in principle all conventional reaction vessels, for example tubular reactors and stirred kettles, it being possible to operate stirred kettles batchwise or continuously and tubular reactors preferably continuously.

The novel process gives solutions of bisepoxide. The solutions of bisepoxide which are obtainable according to the invention may comprise small amounts of monoepoxide, for example of the formula V.1 or V.2

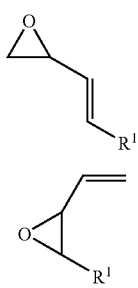

the amount of monoepoxide being, as a rule, less than 8 mol %, based on pure bisepoxide. Bisepoxide can be isolated from the solutions obtainable according to the invention and can be purified.

The present invention furthermore relates to a process for the preparation of dithiol mixtures, also referred to below as novel two-stage process, wherein (a) in a first stage, bisepoxide is prepared by a process as described above and (b) is reacted with $H_2S$ in the presence of at least one basic catalyst without isolation of bisepoxide prepared in stage (a).

In an embodiment of the present invention, solutions of bisepoxides which are obtainable by a process described above are used, and isolation and purification operations are dispensed with.

In an embodiment, reaction is effected in stage (b) with from 1 to 10, preferably from 1 to 2, equivalents, based on one equivalent of epoxide group, of $H_2S$.

Stage (b) of the novel two-stage process is carried out in the presence of at least one basic catalyst.

Suitable basic catalysts are basic alkali metal salts and ammonium salts, for example alkali metal hydroxides, alkali metal carbonates, alkali metal hydrogen sulfides and ammonium hydroxides. Examples of alkali metal cations are $Li^+$, $Na^+$, $K^+$, $Rb^+$ and $Cs^+$, in particular $Na^+$ and $K^+$.

Examples of ammonium ions are not only unsubstituted $NH_4^+$ but also monoalkylated and up to tetraalkylated ammonium, for example $N(R^4)(R^5)(R^6)(R^7)^+$, where $R^4$ to $R^7$ are in each case identical or different and are selected from hydrogen, benzyl, $C_1$-$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl or n-decyl, particularly preferably $C_1$-$C_4$-alkyl, such as methyl, ethyl, n-propyl, isopropyl, n-butyl, isobutyl, sec-butyl and tert-butyl, phenyl or $CH_2$—$CH_2$—OH. Examples are tetramethylammonium, tetraethylammonium, benzyltrimethylammonium, methyldiethanolammonium and n-butyldiethanolammonium.

At least one basic catalyst in stage (b) is preferably selected from alkali metal hydrogen sulfide, alkali metal hydroxide and benzyltri($C_1$-$C_{10}$-alkyl)ammonium hydroxide, and sodium hydrogen sulfide, potassium hydrogen sulfide, sodium hydroxide, potassium hydroxide and benzyltrimethylammonium hydroxide are very particularly preferred.

In an embodiment of the present invention, from $10^{-4}$ to 10, preferably from 0.5 to 5, % by weight, based on bisepoxide, of basic catalyst are used.

In an embodiment of the present invention, stage (b) is carried out at a pressure in the range from 1 to 200, preferably from 1 to 100, particularly preferably from 1 to 10, bar.

In an embodiment of the present invention, stage (b) is carried out at a temperature in the range from −50 to 100° C., preferably from −30 to 80° C., particularly from −10 to 60° C., very particularly preferably from 15 to 35° C.

In an embodiment of the present invention, the novel process is carried out at a pH of from 8 to 13, preferably from 9 to 11.

In an embodiment of the present invention, a bisepoxide solution obtainable after stage (a) of the novel process is used as a starting material, $H_2S$ is added, at least one basic catalyst is then added and the reaction is allowed to proceed.

In an embodiment of the present invention, further solvent selected from the solvents mentioned above under stage (a) can be added in stage (b) of the novel two-stage process.

In an embodiment of the present invention, the duration of reaction is from 10 minutes to 4 hours, preferably from 0.5 hour to 2 hours.

In principle, all conventional reaction vessels are suitable as reaction vessels for carrying out the novel two-stage process, for example tubular reactors and stirred kettles, it being possible to operate stirred kettles batchwise or continuously and tubular reactors preferably continuously. Continuously operated stirred kettle cascades are also conceivable as suitable vessels.

Without wishing to give preference to one theory, it appears conceivable that unreacted peroxide from stage (a) is trapped by any excess $H_2S$ in stage (b).

By carrying out the novel two-stage process, solutions of dithiol mixtures or corresponding salts of dithiols, to which the present invention likewise relates, are obtained. From novel solutions of dithiol mixtures, it is possible to isolate dithiol mixtures or their corresponding salts by methods known per se, for example neutralization or distilling off the solvent or solvents. In order to obtain particularly pure dithiol mixtures, distillation can be effected, for example under reduced pressure.

Via methods known per se, for example chromatography, dithiol mixtures obtainable by the novel process can be separated into erythro- and threo-dithiol, and the enantiomers of threo-dithiol can be separated or increased in concentration by chiral discrimination.

The present invention furthermore relates to dithiol mixtures comprising (A) from 55 to 65, preferably from 59 to 61, mol % of erythro-dithiol and (B) from 35 to 45, preferably from 39 to 41, mol % of threo-dithiol of the formula IV

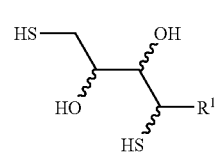

where the variables are defined as above, and corresponding salts of novel dithiol mixtures.

Novel dithiol mixtures comprise compounds which can be represented in Fischer projection as follows:

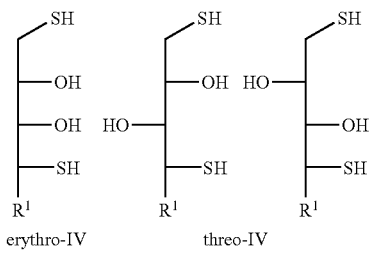

erythro-IV     threo-IV

Novel dithiol mixtures may comprise corresponding salts of erythro-IV and threo-IV.

In an embodiment of the present invention, threo-IV is present in the form of a racemate.

In an embodiment of the present invention, where $R^1$ is selected from unsubstituted or substituted $C_1$-$C_{12}$-alkyl, erythro-IV is present in the form of a racemate.

Novel dithiol mixtures may be contaminated with small amounts of hydroxythiol of the formulae VI.1 or VI.2

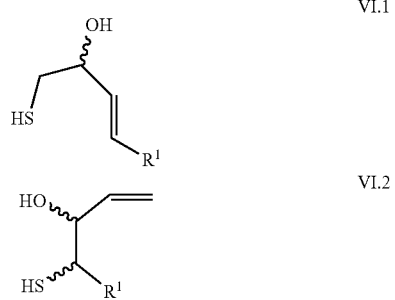

the amount of hydroxythiol generally not exceeding 8 mol %, based on pure dithiol or corresponding salt of dithiol of the formula IV.

Examples of corresponding salts are in particular the mono- and disodium salts, mono- and dipotassium salts and potassium sodium salts of dithiols of the formula IV, and furthermore the corresponding calcium and magnesium salts. The ammonium salts and primary, secondary, tertiary and in particular quaternary mono- and diammonium salts should also be mentioned.

Preferred mono- and diammonium salts have, as cations, those of the formula $N(R^3)(R^4)(R^5)(R^6)^+$, where $R^3$ to $R^6$ in each case are identical or different and are selected from hydrogen, $C_1$-$C_{12}$-alkyl, phenyl or $CH_2$—$CH_2$—OH. Examples are tetramethylammonium, tetraethylammonium, methyldiethanolammonium and n-butyldiethanolammonium.

The present invention furthermore relates to aqueous solutions comprising novel dithiol mixture. Novel aqueous solutions can be obtained, for example, by dissolving novel dithiol mixture or corresponding salt in water. Novel aqueous solutions preferably have a solids content of from 0.1 to 50% by weight.

It has now been found that novel dithiol mixtures and their corresponding salts, for example in the form of their aqueous solution, can be used in an excellent manner for the treatment of hides of dead animals.

The present invention therefore relates to the use of novel dithiol mixtures for the treatment of hides of dead animals.

The present invention furthermore relates to a process for removing horny substances from hides of dead animals using at least one novel dithiol mixture, also referred to below as novel treatment process.

In the context of the present invention, horny substances are understood as meaning calluses, feathers, nail and claw parts and in particular hairs of animals.

Hides of dead animals may still comprise residues of flesh of the relevant dead animals. What is essential to the invention, however, is that they comprise horny substances. The amount of horny substance, based on the total weight of the hide or of the skin or of the skin fur, is not critical. The novel process is suitable both for removing large amounts of horny substance and, for example, for removing small hair residues.

In the context of the present invention, dead animals are understood as meaning not only slaughtered animals or animals killed in another manner but also those animals which have died as a result of accidents, for example traffic accidents or fights with members of their own species or other animals, or through natural causes, such as age or disease.

The hides of dead animals are usually hides of cattle, calves, pigs, goats, sheep, lambs, elks, game, for example stags or roe deer, and furthermore birds, for example ostriches, fish or reptiles, for example snakes.

For carrying out the novel treatment process, it is advantageous to proceed as follows.

At least one novel dithiol mixture is added to at least one hide or hide parts of at least one dead animal.

In general, an amount of from 0.1 to 5% by weight, based on the hide weight or salted weight of the hides, of at least one novel dithiol mixture is sufficient. From 0.5 to 2.5% by weight are preferred and from 0.75 to 1.5% by weight are particularly preferred.

The novel treatment of the hides with at least one novel dithiol mixture is preferably effected during liming or during painting, in particular under hair-destroying or under hair-preserving conditions. During liming or during painting, it is possible to manage with a concentration of less than 1% by weight of $Na_2S$ or NaHS instead of the usual concentration of about 4% by weight of $Na_2S$ or NaHS or even slightly more, with an equivalent or even better effect with regard to the removal of horny substances.

In a variant of the novel process, during the liming, at least one novel dithiol mixture is used together with thiols known from tanning, for example mercaptoethanol or thioglycolic acid. Preferably, less than 0.5% by weight of mercaptoethanol or thioglycolic acid is used.

In a very particularly preferred variant of the novel process, however, it is possible to dispense with the use of $Na_2S$ or NaHS or other foul-smelling sulfur-containing reagents.

In an embodiment of the present invention, hides are treated in an aqueous liquor. The liquor ratio may be from 1:10 to 10:1, preferably from 1:2 to 4:1, particularly preferably up to 3:1, based on the hide weight or salted weight of the hides.

In an embodiment of the present invention, the novel treatment process can be carried out at a pH of from 7 to 14, preferably from 8 to 13, particularly preferably from 9 to 12.5.

For establishing the pH, it is possible to add up to 3% by weight, based on the liquor, of lime (including slaked lime). However, the amount of lime can also be substantially reduced. In a preferred variant of the novel treatment process, the use of lime is dispensed with. In the preferred embodiment, one or more inorganic basic alkali metal compounds are added, for example one or more hydroxides or carbonates of alkali metals, preferably of sodium or potassium, very particularly preferably of sodium. Other suitable inorganic basic alkali metal compounds are alkali metal silicates. It is also possible to add basic amines, for example ammonia, methylamine, dimethylamine, ethylamine or triethylamine, or combinations of alkali metal compound and one or more basic amines.

In addition to water, further organic solvents may also be present in the liquor, for example up to 20% by volume of ethanol or isopropanol.

The novel treatment process can be carried out in vessels which are customary in tanning and in which liming is usually effected. Preferably, the novel treatment process is carried out in rotatable drums having internals. The speed is usually from 0.5 to 100, preferably from 1.5 to 10, particularly preferably up to 4.5, rpm.

The pressure and temperature conditions for carrying out the novel treatment process are generally not critical. The procedure at atmospheric pressure has proven suitable; pressure increased to 10 bar is likewise conceivable. Suitable temperatures are from 10 to 45° C., preferably from 15 to 35° C., particularly preferably from 25 to 30° C.

At least one novel dithiol mixture can be metered at the beginning of the novel treatment process, but it is also possible first to soak the hides under basic conditions and to meter at least one novel dithiol mixture only after some time. The metering can be effected in one step, i.e. the total amount of novel dithiol mixture is metered in one step; however, novel dithiol mixtures can also be metered in portions or continuously.

The novel treatment process can be carried out in a period of from 10 minutes to 48 hours, preferably from 1 to 36, particularly preferably from 3 to 15, hours.

Of course, assistants customary in turning may also be added for carrying out the novel treatment process, for example phosphines, e.g. triphenylphosphine or tris(2-carboxyethyl)phosphine hydrochloride, and furthermore hydroxylamine, urea, guanidine or guanidinium hydrochloride, hydrazine, biocides, enzymes, surfactants and emulsifiers.

Unhaired pelts can be produced in an excellent manner by means of the novel treatment process. Surprisingly, it is also found that the epidermis is completely or at least substantially detached after a short treatment time.

It was furthermore found that pelts produced by the novel treatment process are very suitable for the production of leather. After further processing, in a manner customary in the tannery, of pelts produced by the novel treatment process, i.e. bating, if appropriate deliming, pickling, chromium-free tanning or chrome tanning, retanning and finishing, it is observed that pelts produced by the novel treatment process can be further processed to give leather having an improved yield per unit area and less damage due to swelling compared with leather which is produced from pelts which were unhaired with the aid of, for example, $Na_2S$, NaHS, thioglycolic acid or aminoethanol.

The working examples which follow illustrate the invention.

1. Preparation of a mixture of 40 mol % of erythro-1,4-dimercaptobutane-2,3-diol and 60 mol % of racemic threo-1,4-dimercaptobutane-2,3-diol (a) Preparation of Bisepoxide (a.1)

The following were mixed with one another in a 150 ml glass autoclave having an inlet tube:

42.6 g of acetonitrile, 9 ml of aqueous manganese(II) acetate solution having a concentration of 0.02 mol of Mn/l, 9 ml of 1,4,7-trimethyl-1,4,7-triazacyclononane having a concentration of 0.03 mol/l, 9 ml of aqueous sodium oxalate/oxalic acid buffer (molar ratio: 1:1) having a concentration of 0.06 mol/l of the sum of oxalate and oxalic acid.

The solution thus obtainable was cooled to about −40° C. with the aid of a dry ice/acetone bath. 3.34 g (61.8 mmol) of 1,3-butadiene were then condensed. A temperature of 0° C. was then established with the aid of an ice bath.

16.7 g of 50% by weight aqueous $H_2O_2$ solution (246 mmol of $H_2O_2$) were then pumped in in the course of 1 hour, it being ensured that the temperature did not increase above 25° C. It was observed that the pressure in the autoclave increased to 5.2 bar. Thereafter, the ice bath was removed and stirring was continued for 2 hours at room temperature. Thereafter, a pressure of 3.2 bar was found to have been established.

16.6 g of 50% by weight aqueous $H_2O_2$ solution (244 mmol of $H_2O_2$) were then pumped in, it being ensured that the temperature did not increase above 25° C. It was observed that the pressure in the autoclave increased to 3.8 bar. Thereafter, the ice bath was removed and stirring was effected for 5.5 hours at room temperature. After 5.5 hours, it was found that a pressure of 5 bar had been established.

The pressure was then let down and the composition of the resulting pale solution (94.6 g) was determined by gas chromatography. A content of 58.4 mmol of bisepoxide of the formula VII.1 and 3.4 mmol of vinyloxirane IV.1.1

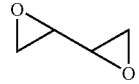

VII.1

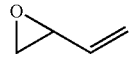

IV.1.1 was determined. The yield of desired bisepoxide VI1.1 was 95.5%.

(a.2)

The reaction from (a.1) was repeated, but stirring was effected for 12 hours at room temperature after pumping in 16.7 g of 50% by weight aqueous $H_2O_2$ solution and removing the ice bath. Further processing was then effected as described under (a.1). Bisepoxide VII.1 was obtained in very good yield.

(b) Preparation of Novel Dithiol Mixture 50 g of the solution resulting from 1 (a.1) were initially taken in a 400 ml glass autoclave and 6 bar $H_2S$ was forced in at room temperature. A solution of 1.04 g of NaOH (solid) in 20 ml of methanol was added with the aid of an HPLC pump. During the addition of methanol/NaOH, a temperature increase from 25 to 35° C. was observed.

The pressure was kept at 6 bar by continuously forcing in $H_2S$. The lines of the HPLC pump were then flushed with 50 ml of acetonitril.

By the end of the reaction, which was evident from a decline in the temperature, the pressure in the autoclave was let down and the autoclave was freed from excess $H_2S$ over a period of 14 hours by passing $N_2$ through the reaction mixture.

83.8 g of a clear solution of dithiol mixture were obtained. The novel dithiol mixture IV.1 obtained was separated by gas chromatography and, according to gas chromatography, had the following composition:

40 mol % of erythro-IV.1

60 mol % of threo-IV.1 in the form of a racemate.

Conditions for the gas chromatography: column: HP-5, length: 30 m, internal diameter=0.25 mm, film thickness 0.25 µm, detector: WLD, Init. T.: 40° C., Init. time: 5 min, rate: 10° C./min, final temperature 290° C., retention time IV.1: 18.00-18.50 min.

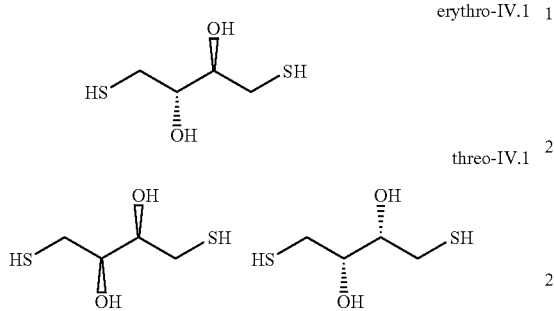

2. Treatment of Pelts with Novel Dithiol Mixture

The values in % by weight are based in each case on the salted weight, unless stated otherwise.

General Pretreatment:

A southern German cattle hide was first presoaked at 28° C. with 200% by weight of water and 0.2% by weight of $C_{15}H_{31}$—O—$(CH_2$—$CH_2$—$O)_7$—H for 10 minutes in a drum with gentle stirring. The liquor was discharged and soaking was then effected with 100% by weight of water, 0.2% by weight of $C_{15}H_{31}$—O—$(CH_2$—$CH_2$—$O)_7$—H and 0.5% by weight of $Na_2CO_3$ with occasional stirring for 19 hours. The liquor was then discharged.

The softened southern German cattle hides were fleshed in the green state (thickness about 4 mm) and the butts of the hides were cut into hide pieces of 2.5 kg green weight each.

Below, the values in % by weight are based in each case on the green weight, unless stated otherwise.

2.1. Liming of Comparative Example C1

For comparative example C1, 100% by weight, based on green weight, were treated in a rotatable 10 l drum having internal baffles in succession with 60 parts by weight of water, 0.8% by weight of NaSH and 3% by weight of slaked lime. 0.75% by weight of sodium sulfide followed at 30 minute intervals. The drum was operated for a further 45 minutes at 15 revolutions per minute. A further 40 parts by weight of water were then metered. After 10 hours at from 23 to 27° C. and 5 revolutions per minute, the experiments were terminated by discharging the liquor and the hides were washed twice for 15 minutes with 150 parts by weight of water.

2.2. Hair-Destroying Liming of the Novel Examples 2.1 to 2.4

In the novel examples 2.1 to 2.4, first 60% by weight of water were added to 100% by weight, based on green weight, in rotatable 10 l drums having internal baffles, and treatment with products, as evident from table 1, was then effected.

TABLE 1

| Example | Amount used [% by weight] | Product | Time [min] |
|---|---|---|---|
| 2.1 | 0.5 | Sodium sulfhydrate (70%) | |
| | 0.5 | Dithiol mixture IV.1 | 60 |
| | 1.2 | Slaked lime | 60 |
| | 1.2 | Slaked lime | 60 |
| 2.2 | 1.0 | Dithiol mixture IV.1 | 60 |
| | 1.2 | Slaked lime | 60 |
| | 1.2 | Slaked lime | |
| 2.3 | 1.5 | Dithiol mixture IV.1 | 60 |
| | 1.2 | Slaked lime | 60 |
| | 1.2 | Slaked lime | 60 |
| 2.4 | 1.0 | Dithiol mixture IV.1 | 60 |
| | 1.0 | Aqueous sodium hydroxide solution (50% by weight) | 30 |
| | 1.0 | Aqueous sodium hydroxide solution (50% by weight) | 30 |
| | 50 | Water | |
| | 0.4 | Aqueous sodium hydroxide solution (50% by weight) | 60 |
| | 50 | Water | 30 |

The drums were operated for a further 45 minutes at 5 revolutions per minute. A further 40% by weight of water were then metered. After 10 hours at from 23 to 27° C. with periodic operation at 3 revolutions per minute over 5 minutes per hour in each case, the experiments were terminated by discharging the liquors, and the pelts obtained were washed twice for 15 minutes each time with 150% by weight of water.

2.3. Assessment of Pelts According to Comparative Example and According to Novel Examples after Liming The pelts treated according to the novel examples were only slightly superior to the hides treated according to comparative example C1 with respect to the swelling but were distinguished by a smoother and flatter grain, in particular the pelts of novel examples 2.3 and 2.4. The epidermis and the hairs with hair root in the pelts according to examples 2.1 to 2.3 had been substantially destroyed and those in pelts according to example 2.4 had been completely destroyed.

We claim:

1. A composition, comprising:

(A) from 55 to 65 mol % of erythro-dithiol of formula erythro-IV:

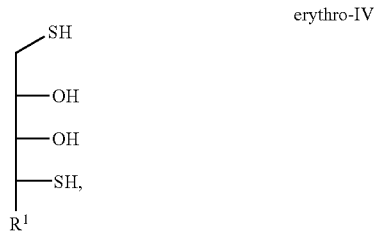

and (B) from 35 to 45 mol % of threo-dithiol of formula threo-IV or threo-IV':

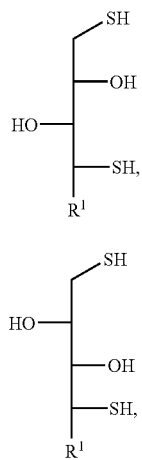

and their corresponding alkali metal salts and ammonium salts, wherein $R^1$ is selected from the group consisting of a hydrogen atom and a $C_1$-$C_{12}$-alkyl group, wherein the $C_1$-$C_{12}$-alkyl group may be unsubstituted or substituted by one or more S—H or O—H groups.

2. The composition according to claim 1, wherein the threo-dithiol of formulae threo-IV and threo-IV' are present as a racemate.

3. An aqueous solution comprising water and the composition of claim 1.

4. A method for treating a hide of a dead animal comprising treating the hide with the composition of claim 1.

5. The method of claim 4, wherein the treating comprises removing horny substances from the hide of the dead animal.

6. A method for treating a hide of a dead animal comprising treating the hide with the composition of claim 2.

7. The method of claim 6, wherein the treating comprises removing horny substances from the hide of the dead animal.

8. A method for treating a hide of a dead animal comprising treating the hide with the aqueous solution of claim 3.

9. The method of claim 8, wherein the treating comprises removing horny substances from the hide of the dead animal.

10. An aqueous solution comprising water and the composition of claim 2.

11. A method for treating a hide of a dead animal comprising treating the hide with the aqueous solution of claim 10.

12. The method of claim 11, wherein the treating comprises removing horny substances from the hide of the dead animal.

13. The composition according to claim 1, wherein $R^1$ is an unsubstituted or substituted $C_1$-$C_{12}$ alkyl goup.

14. The composition according to claim 13, wherein the erythro-dithiol of formula erythro-IV is present as a racemate.

* * * * *